United States Patent [19]

Homsy

[11] Patent Number: 4,778,474
[45] Date of Patent: Oct. 18, 1988

[54] ACETABULAR PROSTHESIS

[76] Inventor: Charles A. Homsy, 11526 Raintree Cir., Houston, Tex. 77024

[21] Appl. No.: 757,150

[22] Filed: Jul. 22, 1985

[30] Foreign Application Priority Data

Nov. 16, 1984 [FR] France .............................. 84 307970
Nov. 24, 1984 [JP] Japan ................................ 59-248562

[51] Int. Cl.⁴ .............................................. A61F 2/34
[52] U.S. Cl. ........................................ 623/22; 623/16; 427/2
[58] Field of Search ............................ 623/22, 23, 16; 128/92 R, 92 XX, 92 XP; 427/2

[56] References Cited

U.S. PATENT DOCUMENTS

| | | | |
|---|---|---|---|
| 3,608,096 | 1/1970 | Link | 623/22 |
| 3,813,699 | 6/1974 | Giliberty | 623/22 |
| 3,906,550 | 9/1975 | Rostoker et al. | 623/22 X |
| 3,992,725 | 11/1976 | Homsy | 623/16 X |
| 4,055,862 | 11/1977 | Farling | 623/22 X |
| 4,164,794 | 8/1979 | Spector et al. | 623/22 |
| 4,336,618 | 6/1982 | Raab | 623/23 |
| 4,351,069 | 9/1982 | Baltintyn et al. | 623/22 |
| 4,531,916 | 7/1985 | Scantlebury et al. | 433/173 |
| 4,547,910 | 10/1985 | Roberts et al. | 623/22 X |

Primary Examiner—Richard J. Apley
Assistant Examiner—Alan W. Cannon
Attorney, Agent, or Firm—Vinson & Elkins

[57] ABSTRACT

An improved acetabular prosthesis (14) is disclosed for use with a femoral head prosthesis (12). The acetabular prosthesis (14) comprises a cup (28) having, in use, sufficient strength to maintain its shape. The exterior surface of the cup (28) is substantially hemispherical. A coating (32) of sufficient thickness is provided on the exterior surface of the cup (28). The coating (32) is sufficiently deformable and has limited elastic memory to mold itself to the particular anatomic geometry or inner contour of the acetabulum. The coating (32) has grooves (36) on its external surfaces.

19 Claims, 1 Drawing Sheet

U.S. Patent
Oct. 18, 1988
4,778,474
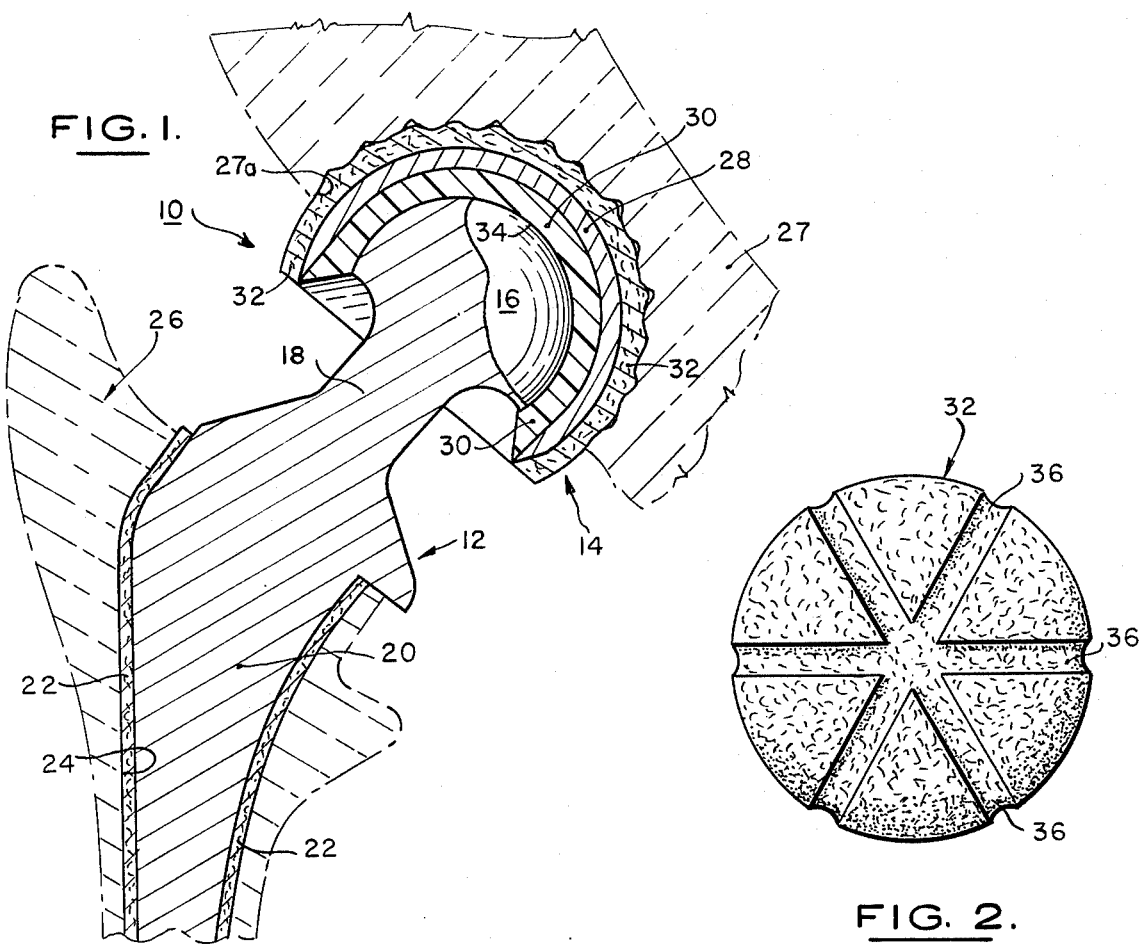
FIG. 1.
FIG. 2.
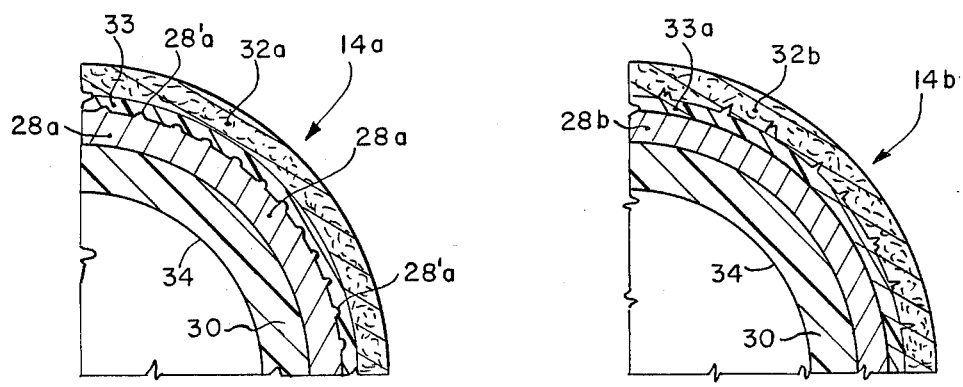
FIG. 3.
FIG. 4.

ACETABULAR PROSTHESIS

CROSS-REFERENCE TO RELATED APPLICATION

This application is a continuation-in-part of application Ser. No. 555,165 filed Nov. 25, 1983, now abandoned.

BACKGROUND OF THE INVENTION

1. Field Of The Invention

The present invention relates to an improved acetabular prosthesis for use in a total hip joint prosthesis which uses materials that conform and adapt to the shape of the natural acetabulum of the patient.

2. Description Of The Prior Art

A total hip prosthesis commonly includes two components: a femoral-head prosthesis and an acetabular prosthesis.

A known femoral-head prosthesis includes a ball-type head which has the shape of a hemisphere. A stem extends from the head and is adapted for insertion into a femoral medullary canal. The stem is preferably coated with a stabilizing material, either an acrylic cement or a low modulus tissue ingrowth material, such as is disclosed in U.S. Pat. No. 3,992,725 dated Nov. 23, 1976.

One known type of acetabular prosthesis includes a hemispherical cup which is fixed within the natural acetabulum with an acrylic cement and through anchoring holes in the pelvis. Screws or the like extend from the convex side of the cup and engage the holes in the pelvis.

But, when the cement non-uniformly transfers load stresses, there can result a loss of bone leading to a gradual degradation of the useful life of the implanted prosthesis.

An acetabular prosthesis is also known which has a metallic hemispherical cup which is not mechanically secured to the pelvis. The cup has an internal concave surface which is lined with a biocompatible and wear resistant polymer such as ultra high molecular weight polyethylene. Articulation in this implant takes place on one hand between the head of the femoral-head prosthesis and the lining of the cup, and on the other hand between the polished convex surface of the cup and the natural acetabulum.

While such an unfixed acetabular prosthesis does not require holes in the pelvis, it may develop serious problems due to the fact that the exterior of the cup is hemispherical and the natural acetabulum in which the cup articulates is not a true portion of a sphere because it may have natural or disease-caused irregularities, which can cause loads transmitted through the hip joint to become localized and abnormal, thereby damaging the natural acetabulum. Such localized load is also understood to be a cause of pain.

This problem is described in U.S. Pat. No. 4,318,191, wherein a unitary hip joint prosthesis is described having a compliant metal head which is intended to conform and adjust to the shape of the natural acetabulum and thereby to avoid abnormal stress loadings. This metal head leaves much to be desired as to its ability to adjust to irregularities in the acetabulum geometry and to protect the acetabulum against abnormal dynamic loads which are normally transmitted by the hip joint.

Another prosthetic device is described in U.S. Pat. No. 4,164,794 dated Aug. 21, 1979 and has a coating particularly designed for use where long-term bone fixation is desired by tissue ingrowth into and through the coating with subsequent remodelling to bone. The porosity and other characteristics of the coating are designed to promote tissue ingrowth so that stresses are transferred to bone spicules within the pores. A relatively high modulus of elasticity is provided in U.S. Pat. No. 4,164,794 that is conductive to bone formation without micromotion occurring with loading of the prosthesis.

SUMMARY OF THE INVENTION

It is therefore an object of the present invention to provide an improved acetabular prosthesis which avoids non-uniform and abnormal load transmission to the natural acetabulum, and which does not require pelvic fixation.

A further object is to provide an improved acetabular prosthesis which maintains a uniform engagement with the surface of the natural acetabulum.

The above and other objects are achieved by providing an improved acetabular prosthesis for use with a femoral head prosthesis. The acetabular prosthesis comprises a cup having, in use, sufficient strength to maintain its shape. A bio-compatible coating of sufficient thickness is provided on the exterior surface of the cup. The coating is sufficiently deformable and has limited elastic memory to allow it to mold itself into the particular anatomic geometry or adjacent contour of the acetabulum. An inner wear-resistant lining is on the inner surface of the cup.

Preferably, said coating is polytetrafluoroethylene, which has a porosity in the range from forty percent (40%) to ninety percent (90%), a thickness in the range from one millimeter (1 mm) to ten millimeters (10 mm), and a plurality of grooves on its exterior surface to allow, in use, bulk movement of synovial fluid therethrough.

BRIEF DESCRIPTION OF THE DRAWINGS

Other objects, features, and advantages of this invention will become more apparent after referring to the following specification and drawings.

FIG. 1 is a partial sectional view of a hip joint prosthesis featuring the improved acetabular prosthesis of this invention, and illustrating the relative positions of the femur and pelvis.

FIG. 2 is a plan view of the external surface of the acetabular prosthesis shown in FIG. 1.

FIG. 3 is a partial sectional view of a modified form of the acetabular prosthesis shown in FIG. 1.

FIG. 4 is a partial sectional view of another modified form of the acetabular prosthesis shown in FIG. 3.

DESCRIPTION OF PREFERRED EMBODIMENT

With particular reference now to the drawings, the hip joint prosthesis, generally designated as 10, includes two components: a femoral-head prosthesis 12, and an acetabular prosthesis 14.

Prosthesis 12 is preferably of the type described in copending application Ser. No. 476,117 filed Mar. 17, 1983. It includes a polished hemisphere ball 16, a neck 18, and a stem 20, which has a coating 22 bonded to its exterior surface. Coating 22 is preferably a tissue ingrowth material, such as is disclosed in aforesaid U.S. Pat. No. 3,992,725. Stem 20 is inserted into medullary canal 24 of femur 26. Coating 22 serves to stabilize or fix prosthesis 12 in femur 26.

Prosthesis 14 includes a cup 28 which is made of a sufficiently strong material which can be an implantable metal, polysulfone, polycarbonate, or a polyacetal polymer. Prosthesis 14 is inserted into the acetabulum 27a of pelvis 27. The internal surface of cup 28 is provided with a lining 30, and the external surface of cup 28 is covered by a coating 32. Lining 30 is preferably made of a suitable biocompatible wear-resistant material, such as ultra-high molecular weight polyethylene. Lining 30 is suitably secured within cup 28 by a press fit. Lining 30 has an interior surface 34 which has at least in part a hemispherical shape and in which ball 16 articulates.

Coating 32 is a deformable material having little or low elastic memory. Coating 32 is preferably a coating of porous polytetrafluoroethylene exhibiting a porosity in the range from forty percent (40%) to ninety percent (90%), and preferably around sixty percent (60%) porosity. It is also preferred that interconnecting pores have a size ranging from about ten (10) to fifty (50) microns so that the ingrowth of tissue into the porosity of coating 32 is minimized. Coating 32 preferably has a thickness in the range of one to ten millimeters (1-10 mm); the thicker coatings being used for a natural acetabulum having variations which require such thickness for the self-molding of the coating therein i.e., for the coating to deform and adapt itself to the natural shape or contour of acetabulum 27a. The porous polytetrafluoroethylene coating 32 may preferably be a material such as described in aforesaid copending application Ser. No. 204,528, filed Nov. 6, 1980, abandoned and refiled as continuation-in-part application Ser. No. 549,805 on Nov. 8, 1983, now U.S. Pat. No. 4,576,608, issued Mar. 18, 1986. Fluorinated ethylene propylene is a preferred agent for the preferred coating 32. Another appropriate material for coating 32 is the material disclosed in said U.S. Pat. No. 3,992,725. Such material can be also bonded to cup 28 by the same bonding agent as the preferred material.

The acetabulum or socket receiving acetabular prosthesis 14 has natural cartilage therein which is in contact with prosthesis 14, and coating 32 is designed particularly to deform or self-mold substantially inelastically to the specific shape or contour of the receiving natural acetabulum. It is highly desirable for coating 32 to have a limited memory upon any deformation in order to have a sufficient rigidity, and thus it is substantially inelastic. The porosity of coating 32 provides the inelastic or limited memory feature.

Natural cartilage which will be in an apposed relation to prosthesis 14 has a relatively low modulus of elasticity and it is desirable for coating 32 to have a modulus of elasticity similar to the cartilage. It is understood that cartilage will have a range of low elasticity depending on such factors as the age of the person receiving the implant, and the intrinsic water content of the cartilage as this is an indication of the degree of cartilage degeneration.

Natural cartilage is comprised of both solid and liquid portions and the elasticity of cartilage is generally measured as the "modulus of elasticity in compression" which is a measurement of its bulk properties under compression.

The modulus of elasticity of natural cartilage is around one (1) to two (2) megapascals (MPa). Coating 32 preferably has a modulus of elasticity in compression less than around four (4) MPa which is suitable to provide the necessary softness and yet sufficient rigidity so that the cartilage is not abraded or deteriorated by coating 32.

An advantage in coating 32 having a modulus of elasticity similar to that of the adjacent cartilage is that it may act in a manner similar to the natural cartilage adjacent the natural femoral head before the head was removed. A function of the natural cartilage on the femoral head and within the acetabulum is to assist in the dissipation of impact loads during walking, running, and similar physical operations. Therefore, coating 32 is particularly selected to have overall properties that (1) avoid mechanical abuse of the retained cartilage in the acetabulum, and (2) provide impact dissipation and load distribution to the reconstructed joint similar to that existing in a normal, natural joint with natural cartilage. It is pointed out, however, that the modulus of elasticity is not uniform for the entire coating 32 and may vary depending on the amount of compression at a particular location. Thus, the thickness of coating 32 and its resilience are selected to provide the desired elasticity for maximum compression.

Coating 32 comprising the present invention is designed to have a softness generally similar to the apposed cartilage, and also to simulate other mechanical characteristics of the cartilage against which it is apposed. It is noted that the coating is not designed for any ingrowth of tissue and does not have any substantial capability for such ingrowth.

As shown in FIG. 2, coating 32 preferably includes a plurality of rounded grooves 36 on its exterior surface, to allow synovial fluid to flow therethrough. The low or limited elastic memory of coating 32, even when compressed, allows it to be compliant with the apposed natural cartilage so that the coating's deformation continuously accommodates the topography or conforms to the adjacent contour of the cartilage contacted. In the deformed state of coating 32, further loading is attenuated by the elasticity of coating 32 and of the cartilage, thereby simulating continuous impact absorption as in a natural joint. Further, this uniform loading allows the joint to function almost as a natural joint. Also the normal perfusion of nutrients into the cartilage assists in maintaining the natural health of the joint.

In FIG. 3 is shown a modified acetabular prosthesis 14a which includes a cup 28a with an interior lining 30 and an exterior coating 32a, as shown and described with reference to FIG. 1. However, coating 32a is not bonded directly to the exterior surface of cup 28a but to an intermediate layer 33 of medical grade elastomer. Attachment of layer 33 to cup 28a is by mechanical interlocking of the elastomer to a roughness 28'a on the exterior surface of cup 28a, and attachment of layer 33 to coating 32a is by mechanical interlocking to the surface porosity of coating 32a.

Another modified acetabular prosthesis 14b, shown in FIG. 4, is similar to the embodiment of FIG. 3, except that a portion of coating 32b, adjacent to the exterior surface of cup 28b, is now impregnated with a medical grade elastomer 33a. Attachment of the impregnated coating 32b to cup 28 is by mechanical interlocking of the elastomer with the surface of cup 28b. In order to achieve this structure, the portion of coating 32b which is impregnated with the medical grade elastomer is made to have a porosity of seventy percent (70%) to ninety percent (90%). The remainder of coating 32b exhibits a porosity in the range from forty percent (40%) to ninety percent (90%); sixty percent (60%) porosity is preferred.

In the modified forms of FIGS. 3 and 4, it is preferred that the medical grade elastomer be a suitable medical grade silicone. These modified forms provide additional resiliency to the prosthetic joint which will aid in the absorption of shock energy during ambulation of the patient. The low or limited elastic memory of coating 32, even when compressed, allows it to be compliant with the apposed natural cartilage so that the deformation of the cartilage is the means of perfusing nutrients into the cartilage.

As indicated previously, the amount of compression for coating 32 will vary at different locations across the area of the implant. While coating 32 under normal conditions would not be compressed so that all of its porosity is utilized, it is possible that compression could occur to cause the modulus of elasticity of the compressed material to increase above the preferred maximum. However, by selecting an appropriate thickness for layer 33 or 33a of elastomeric material, coating 32 can always retain at least a residual modulus of elasticity which will be below the preferred maximum. Thus, the use of coating 32 having a silicon rubber impregnated layer therein of a predetermined thickness provides an upper limit to the modulus of elasticity of coating 32 that is reached.

The modified acetabular prostheses 14a and 14b accommodate local deviations on the order of one millimeter (1 mm) from the non-hemispherical shape of the natural acetabulum 27a. The larger end of the thickness range for coating 32 allows it to self-mold to an overall distorted shape of the natural acetabulum. Although coating 32 has a low elastic memory in order to deform and mold itself to the acetabular cavity, it should preferably also possess a low degree of elasticity which would allow it to absorb energy during the cyclic impositions of loads thereon.

While preferred embodiments of the present invention have been illustrated in detail, it is apparent that modifications and adaptations of the preferred embodiments will occur to those skilled in the art. However, it is to be expressly understood that such modifications and adaptations are within the spirit and scope of the present invention as set forth in the following claims.

What is claimed is:

1. An improved acetabular prosthesis for fitting over a hemispherical ball of a femoral-head prosthesis and adapted to fit within the acetabulum in opposed contacting relation to the natural cartilage of the acetabulum; said prosthesis comprising:
   a generally rigid cup having an internal concave surface and a external convex surface;
   a lining over the internal concave surface of said cup formed of a wear-resistant material and fitting against said hemispherical ball; and
   a biocompatible pliant coating over the external convex surface of said cup formed of a deformable porous material having a porosity in the range of 40% to 90% and having interconnecting pores of a size from about 10 to 50 microns for minimizing the ingrowth of tissue into the pores;
   said coating having a relatively low elastic memory and a relatively low modulus of elasticity generally similar to the cartilage of the acetabulum, said relatively low elastic memory and relatively low modulus of elasticity upon compression and deformation of the coating against the natural cartilage of the acetabulum permitting said coating to mold itself to the inner contour of the cartilage and natural acetabulum for continuously commodating the contour of the acetabulum, said relatively low elastic memory and relatively low modulus of elasticity providing sufficient softness in the coating so that the adjacent cartilage is not abraded or deteriorated therefrom.

2. A prosthesis according to claim 1, characterized in that said cup is made of a material selected from the group consisting of metal, polysulfone polymer, polycarbonate polymer, and polyacetal polymer.

3. A prosthesis according to claim 1, characterized in that the coating on said cup is porous polytetrafluoroethylene having a porosity in the range from 40% to 90%.

4. A prosthesis according to claim 3, characterized in that said coating has a porosity of approximately 60%.

5. A prosthesis according to claim 1, characterized in that said coating has a thickness in the range from 1 to 10 mm.

6. A prosthesis according to claim 1, characterized in that said coating has a plurality of grooves on its exterior surface to allow, in use, bulk movement of synovial fluid therethrough.

7. A prosthesis according to claim 3, characterized in that said coating is bonded to said cup with fluorinated ethylene propylene.

8. A prosthesis according to claim 1, characterized in that a layer of medical grade elastomer lies between the exterior of said cup and said coating.

9. A prosthesis according to claim 8, characterized in that said layer is mechanically interlocked to said cup and to said coating.

10. A prosthesis according to claim 8, characterized in that said layer is impregnated into the interior of said coating.

11. A prosthesis according to claim 8, characterized in that said layer is a medical grade silicone.

12. An improved acetabular prosthesis for fitting over a hemispherical ball of a femoral-head prosthesis and adapted to fit within the acetabulum in opposed contacting relation to the natural cartilage of the acetabulum; said prosthesis comprising:
    a generally rigid cup having an internal concave surface and an external convex surface;
    a lining over the internal concave surface of said cup formed of a wear-resistant material and fitting in contact with said hemispherical ball; and
    a biocompatible coating over the external convex surface of said cup formed of a deformable porous material having a relatively low elastic memory and a relatively low modulus of elasticity generally similar to the cartilage of the acetabulum to allow it to mold itself to the inner contour of the natural acetabulum, said coating having pores of a size between about 10 and 50 microns to minimize any tissue ingrowth from said acetabulum.

13. An improved acetabular prosthesis as set forth in claim 12 wherein said coating has an aggregate modulus of elasticity in compression less than around 4 MPa.

14. An improved acetabular prosthesis as set forth in claim 12 wherein a layer of medical grade elastomer is positioned between said convex surface of the cup and said coating.

15. An improved acetabular prosthesis as set forth in claim 13 wherein said coating is a porous polytetrafluoroethylene having a porosity in the range from 40% to 90% and a thickness in the range from 1 to 10 mm.

16. An improved acetabular prosthesis for fitting over a hemispherical ball of a femoral-head prosthesis and adapted to fit within the acetabulum in apposed contacting relation to the natural cartilage of the acetabulum; said prosthesis comprising:

- a generally rigid cup having an internal concave surface and an external convex surface;
- a lining over the internal concave surface of said cup formed of a wear-resistant material and fitting in contact with said hemispherical ball;
- a porous biocompatible coating over the external convex surface of said cup formed of a deformable material having a relatively low elastic memory and a modulus of elasticity generally similar to the cartilage of the acetabulum and less than around four megapascals (4 MPa) to allow it to mold itself to the inner contour of the natural acetabulum; and
- a layer of medical grade elastomer positioned between the exterior of said cup and said coating, said elastomer having a thickness adequate to provide a predetermined resilience for said coating under a predetermined compression thereof.

17. An improved acetabular prosthesis as set forth in claim 16 wherein said porous coating has a porosity of between around 40% to 90% and has an internal pore size of around ten to fifty microns.

18. An improved acetabular prosthesis for fitting over a hemispherical ball of a femoral-head prosthesis and adapted to fit within the acetabulum in opposed contacting relation to the natural cartilage of the acetabulum; said prosthesis comprising:

- a generally rigid cup having an internal concave surface and an external convex surface;
- a-lining over the internal concave surface of said cup formed of a wear-resistant material and fitting against said hemispherical ball; and
- a biocompatible pliant coating over the external convex surface of said cup formed of a deformable porous material having a relatively low elastic memory and a relatively low modulus of elasticity less than around 4 megapascals and generally similar to the cartilage of the acetabulum;
- said coating having a porosity in the range of 40% to 90% and having interconnecting pores of a size from about 10 to 50 microns for minizing the ingrowth of tissue into the pores, said relatively low elastic memory and relatively low modulus of elasticity upon compression and deformation of the coating against the natural cartilage of the acetabulum permitting said coating to mold itself to the inner contour of the cartilage and natural acetabulum for continuously accommodating the contour of the acetabulum; and
- means in said coating to permit the flow of synovial fluid into the adjacent cartilage even upon deformation of the coating.

19. An improved acetabulum prosthesis as set forth in claim 18 wherein said means in said coating to permit the flow of synovial fluid into the adjacent cartilage even upon deformation of the coating comprises a plurality of grooves on the external surface of the coating.

* * * * *